(12) United States Patent
Salter et al.

(10) Patent No.: US 10,052,396 B2
(45) Date of Patent: Aug. 21, 2018

(54) ULTRAVIOLET B LIGHTING SYSTEM FOR A MOTOR VEHICLE

(71) Applicant: FORD GLOBAL TECHNOLOGIES, LLC, Dearborn, MI (US)

(72) Inventors: Stuart C. Salter, White Lake, MI (US); Kristin Ann Hellman, Walled Lake, MI (US); Annette Lynn Huebner, White Lake, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 89 days.

(21) Appl. No.: 15/209,149

(22) Filed: Jul. 13, 2016

(65) Prior Publication Data

US 2018/0015192 A1     Jan. 18, 2018

(51) Int. Cl.
| | |
|---|---|
| *B60Q 3/68* | (2017.01) |
| *A61L 2/10* | (2006.01) |
| *A61N 5/06* | (2006.01) |
| *F21V 23/00* | (2015.01) |
| *A61L 2/00* | (2006.01) |
| *A61L 9/20* | (2006.01) |

(52) U.S. Cl.
CPC ............... *A61L 2/10* (2013.01); *A61L 2/0047* (2013.01); *A61L 9/20* (2013.01); *A61N 5/0613* (2013.01); *B60Q 3/68* (2017.02); *F21V 23/005* (2013.01); *A61L 2202/11* (2013.01); *A61L 2202/14* (2013.01); *A61L 2202/25* (2013.01); *A61L 2209/11* (2013.01); *A61L 2209/12* (2013.01); *A61N 2005/0652* (2013.01); *A61N 2005/0661* (2013.01)

(58) Field of Classification Search
CPC .... A61L 2/10; A61L 2202/11; A61L 2202/25; A61N 5/0613; A61N 2005/0652; A61N 2005/0661; B60Q 3/008; B60Q 3/00; B60Q 3/68; B60Q 3/74; B60Q 3/20; F21V 23/005
See application file for complete search history.

(56) References Cited

U.S. PATENT DOCUMENTS

| | | | | |
|---|---|---|---|---|
| 6,819,249 | B1 * | 11/2004 | Papp | B60N 2/002 |
| | | | | 307/10.1 |
| 9,789,215 | B1 * | 10/2017 | Collins | A61L 2/10 |
| 2003/0093200 | A1 * | 5/2003 | Gutta | G08B 13/19602 |
| | | | | 701/45 |
| 2007/0053188 | A1 * | 3/2007 | New | A61L 9/20 |
| | | | | 362/276 |

(Continued)

FOREIGN PATENT DOCUMENTS

| | | |
|---|---|---|
| CN | 1570465 A | 1/2005 |
| CN | 204246538 U | 12/2012 |

(Continued)

OTHER PUBLICATIONS

English Machine Translation of CN103316375A.

(Continued)

*Primary Examiner* — Bao Q Truong
(74) *Attorney, Agent, or Firm* — Vichit Chea; King & Schickli, LLC

(57) ABSTRACT

A UVB lighting system for a motor vehicle includes a printed circuit board including a UVB light source and a map light. A controller operates the system. A related method is also disclosed.

20 Claims, 5 Drawing Sheets

(56) References Cited

U.S. PATENT DOCUMENTS

2010/0140511 A1    6/2010    Auday et al.
2016/0089548 A1    3/2016    Kaas

FOREIGN PATENT DOCUMENTS

| CN | 103316375 A | 9/2013 |
|---|---|---|
| JP | 20122254673 A | 12/2012 |
| KR | 200400220 Y1 | 11/2005 |
| KR | 20150017544 A | 2/2015 |
| WO | 2011053072 A2 | 5/2011 |

OTHER PUBLICATIONS

English Machine Translation of CN1570465A.
English Machine Translation of CN204246538U.
English Machine Translation of JP2012254673A.
English Machine Translation of KR200400220Y1.
English Machine Translation of KR20150017544A.
English Machine Translation of WO2011053072A2.

\* cited by examiner

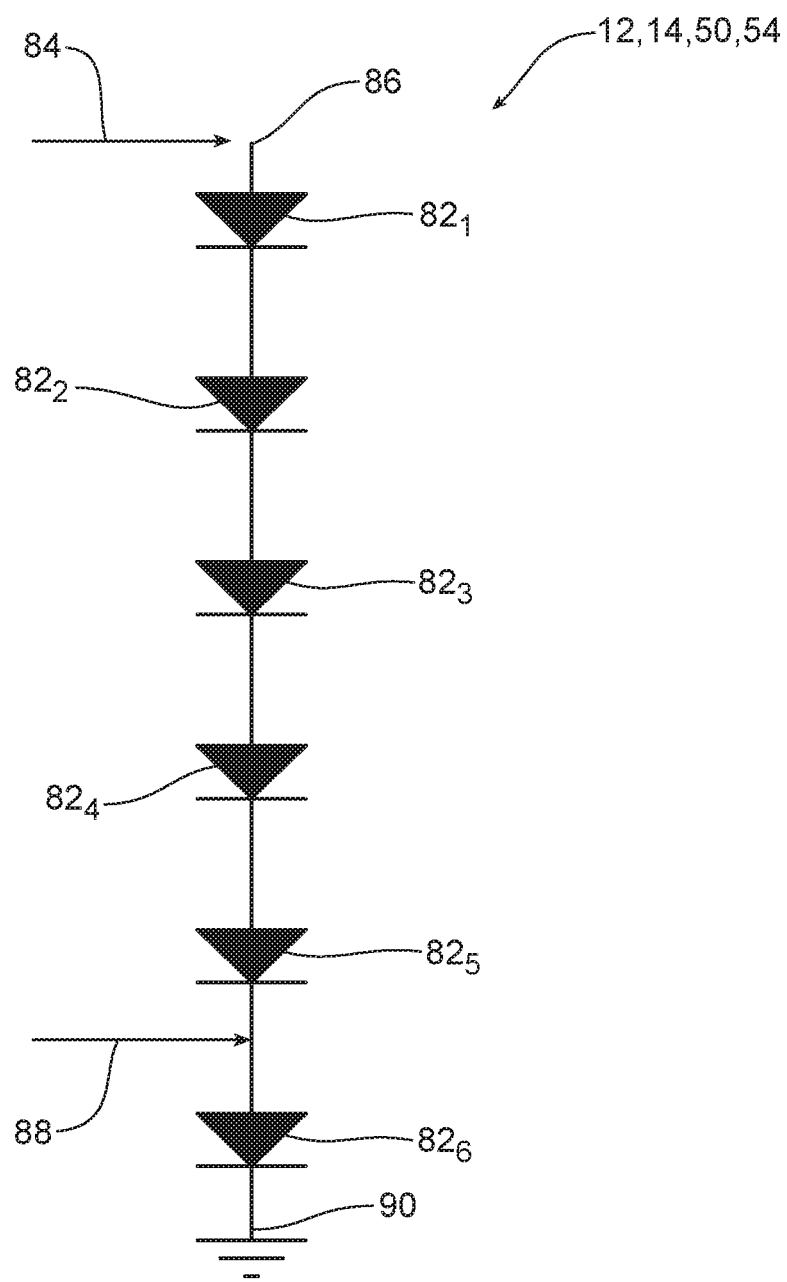

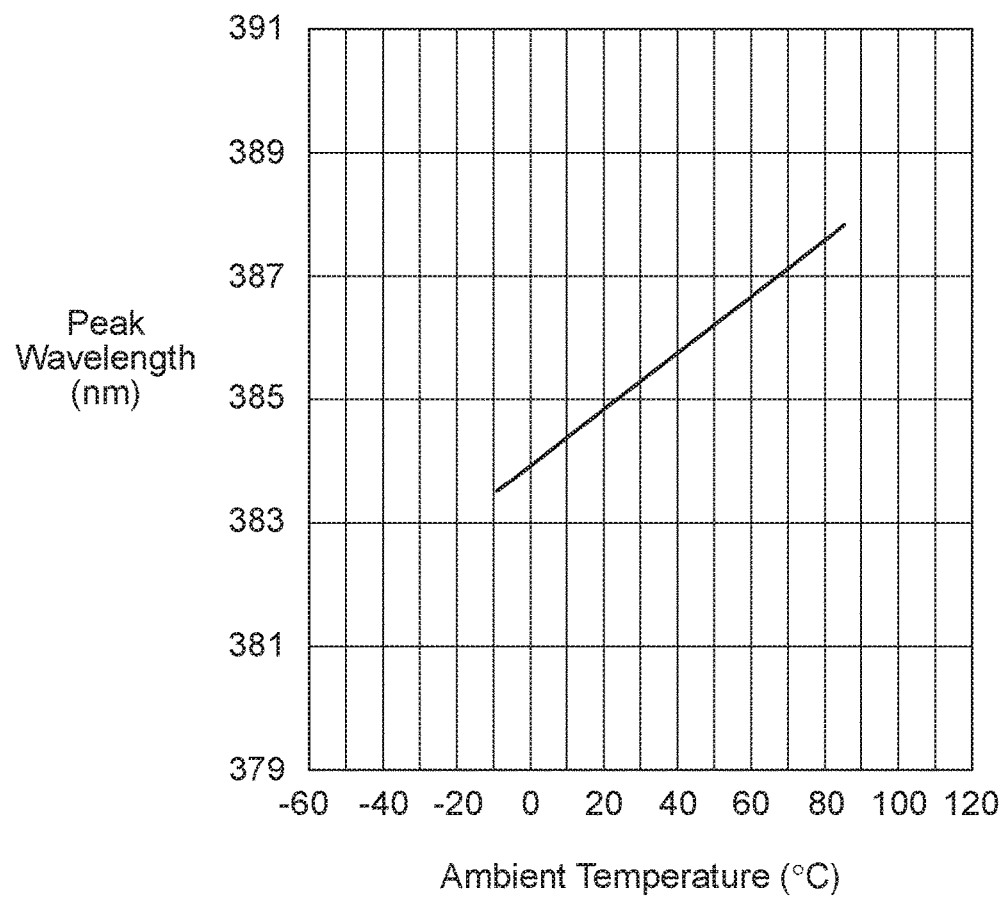

ULTRAVIOLET B LIGHTING SYSTEM FOR A MOTOR VEHICLE

TECHNICAL FIELD

This document relates generally to the motor vehicle equipment field and, more particularly, to an ultraviolet B lighting system for a motor vehicle that is adapted to both promote vitamin D production in human occupants of the motor vehicle as well as kill germs on the human interface surfaces of the interior of the passenger compartment of the motor vehicle.

BACKGROUND

Most humans depend on the sun in order to promote vitamin D production within their bodies. Skin pigment, the use of sunscreen, aging, time of day and season as well as the latitude dramatically affect vitamin D synthesis.

For many individuals it would be helpful to have a low cost vitamin D light source in the passenger compartment of a motor vehicle in order to provide ultraviolet B (UVB) rays to stimulate vitamin D production. Further, such UVB rays also provide the additional benefit of killing germs on the exposed, human interface surfaces of the interior of the motor vehicle subject to the UVB radiation.

SUMMARY

In accordance with the purposes and benefits described herein, a UVB lighting system is provided for a motor vehicle. That UVB lighting system comprises a printed circuit board including a UVB light source and a map light. In addition, the UVB lighting system may include a controller configured to activate the UVB light source for a predetermined operating cycle and to flash the map light when the operating cycle is completed.

Still further, the UVB lighting system may include a UVB indicator lamp on the printed circuit board and the controller may be configured to activate the UVB indicator lamp when the UVB light source is activated so as to provide a visual indication of UVB light source activation.

Still further, the UVB lighting system may include a child detection device and the controller may be connected to the child detection device and configured to prevent activation of the UVB light source when a child is detected in a passenger compartment of the motor vehicle. In one of many possible embodiments, the child detection device may be a seat weight sensor. In another of many possible embodiments, the child detection device may be an imaging device such as a camera.

A controller may be connected to the visual imaging device and configured to adjust an operating cycle of the UVB light source for makeup or sunscreen worn by an occupant of a passenger compartment of a motor vehicle.

In still another of many possible embodiments, the controller of the UVB lighting system may be configured to customize an operating cycle of the UVB light source to a particular operator.

In still other of many possible embodiments, the UVB light source may comprise a plurality of UVB light emitting diodes. The plurality of UVB light emitting diodes may be provided in series. Further, the UVB lighting system may include a first power input at a first end of the plurality of UVB light emitting diodes and a second power input between the first end and a second end of the plurality of UVB light emitting diodes. In addition, the controller may be configured to feed power to the plurality of UVB light emitting diodes (a) via the first power input for sanitation or disinfection of the passenger compartment of the motor vehicle and (b) via the second power input for promoting vitamin D production.

In accordance with still another aspect, a method is disclosed for providing UVB lighting in a motor vehicle. That method may comprise the steps of: (a) locating a UVB light source along a roof panel of the motor vehicle, (b) activating, by a controller, the UVB light source for a predetermined operating cycle and (c) flashing, by the controller, a map light when the operating cycle is completed.

The method may further include the step of activating, by the controller, a UVB indicator lamp when the UVB light source is activated so as to provide a visual indication of the UVB light source activation. In addition, the method may include the step of detecting, by a child detection device, a child in a passenger compartment of the motor vehicle. This may be done in conjunction with the step of preventing, by the controller, activation of the UVB light source when a child is detected.

Still further, the method may include the steps of detecting, by visual imaging device, makeup or sunscreen on a face of a vehicle occupant and adjusting, by the controller, the predetermined operating cycle of the UVB light source for detected makeup or sunscreen worn on the face of the vehicle occupant.

Still further, the method may include the step of customizing, by the controller, the predetermined operating cycle of the UVB light source for a particular operator. In addition, the method may include the step of operating, by the controller, the UVB light source at a first temperature and a first intensity when sanitizing a passenger compartment of the motor vehicle. Further, the method may include the step of operating, but the controller, the UVB light source at a second temperature and a second intensity when promoting vitamin D production of an occupant of the motor vehicle.

In addition, the method may include the step of confirming, by the controller, that the motor vehicle is unoccupied and locked before activating said UVB light source to sanitize a passenger compartment of the motor vehicle.

In the following description, there are shown and described several preferred embodiments of the UVB lighting system. As it should be realized, the UVB lighting system is capable of other, different embodiments and its several details are capable of modification in various, obvious aspects all without departing from the UVB lighting system as set forth and described in the following claims. Accordingly, the drawings and descriptions should be regarded as illustrative in nature and not as restrictive.

BRIEF DESCRIPTION OF THE DRAWING FIGURES

The accompanying drawing figures incorporated herein and forming a part of the specification, illustrate several aspects of the UVB lighting system and together with the description serve to explain certain principles thereof. In the drawing figures:

FIG. 4 is a schematic block diagram of a UVB light source of a type that may be utilized in the UVB lighting system illustrated in FIG. 1.

FIG. 5 is a plot of peak wavelength versus ambient temperature for one possible UVB light emitting diode such as may be utilized in the UVB lighting system illustrated in FIG. 1.

Reference will now be made in detail to the present preferred embodiments of the UVB lighting system and the related method of providing UVB lighting in a motor vehicle. Example embodiments are illustrated in the accompanying drawing figures.

DETAILED DESCRIPTION

Figure 1:
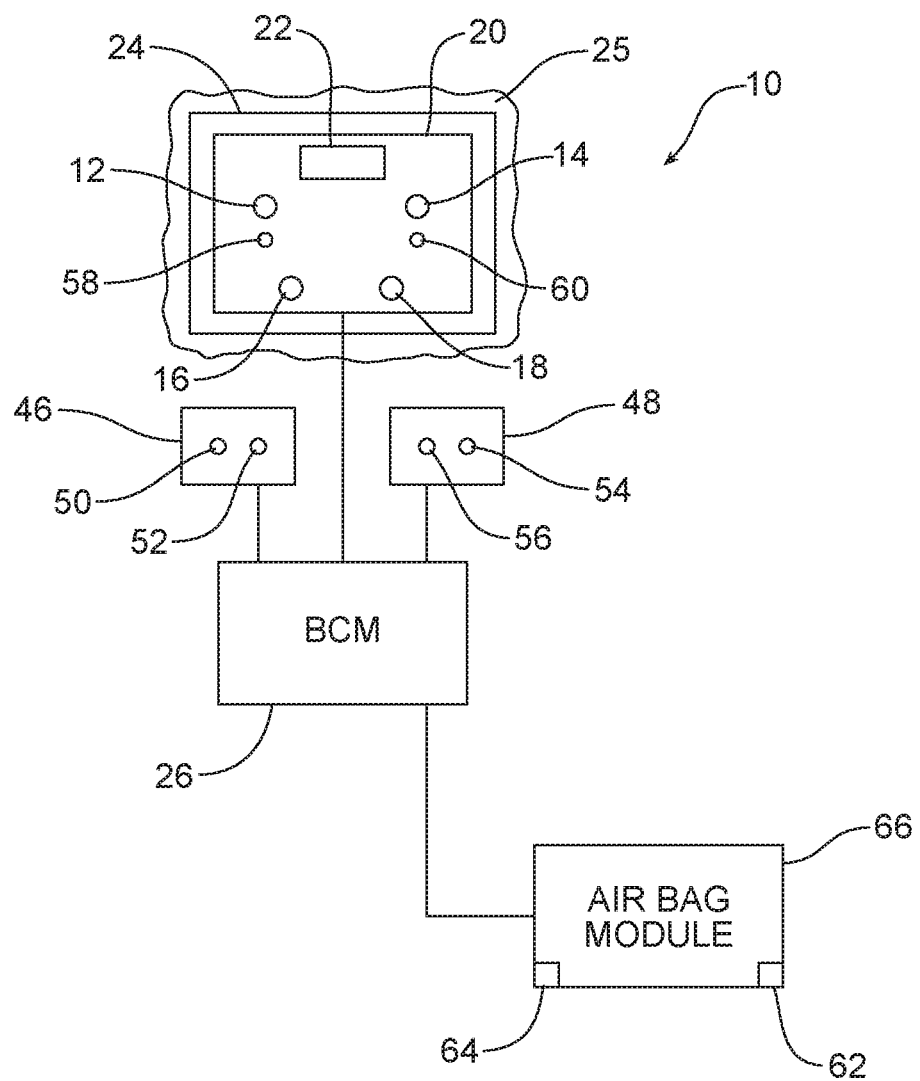
FIG. 1 is a schematic block diagram of the UVB lighting system.

Reference is now made to FIG. 1 illustrating just one of the many possible embodiments of a UVB lighting system 10 for a motor vehicle. Such a UVB lighting system 10 is adapted to emit UVB light at wavelengths of between about 280 and 315 nanometers. UVB light functions to promote the production of vitamin D in humans. Vitamin D is an essential ingredient for human health. Further, it should be appreciated that UVB light also has a disinfecting quality and UVB light of a wavelength of about 280 nm is particularly useful in killing germs. Thus, it should be appreciated that the UVB lighting system 10 provides multiple benefits, that is, the production of vitamin D in the humans occupying the passenger compartment of the motor vehicle as well as the killing of germs on the exposed surfaces in the passenger compartment of the motor vehicle with which the humans interface.

As illustrated in FIG. 1, the UVB lighting system 10 may include a first UVB light source 12, a second UVB light source 14, a first map light 16 and a second map light 18 all provided on the same printed circuit board 20.

As further illustrated, a courtesy light 22 may also be provided on the circuit board 20. The printed circuit board 20, including the first UVB light source 12, second UVB light source 14, first map light 16, second map light 18 and courtesy light 22 carried thereon, may be a part of a lighting module 24 housed in a roof console on a roof panel 25 of the motor vehicle immediately behind the windshield.

Figure 2:
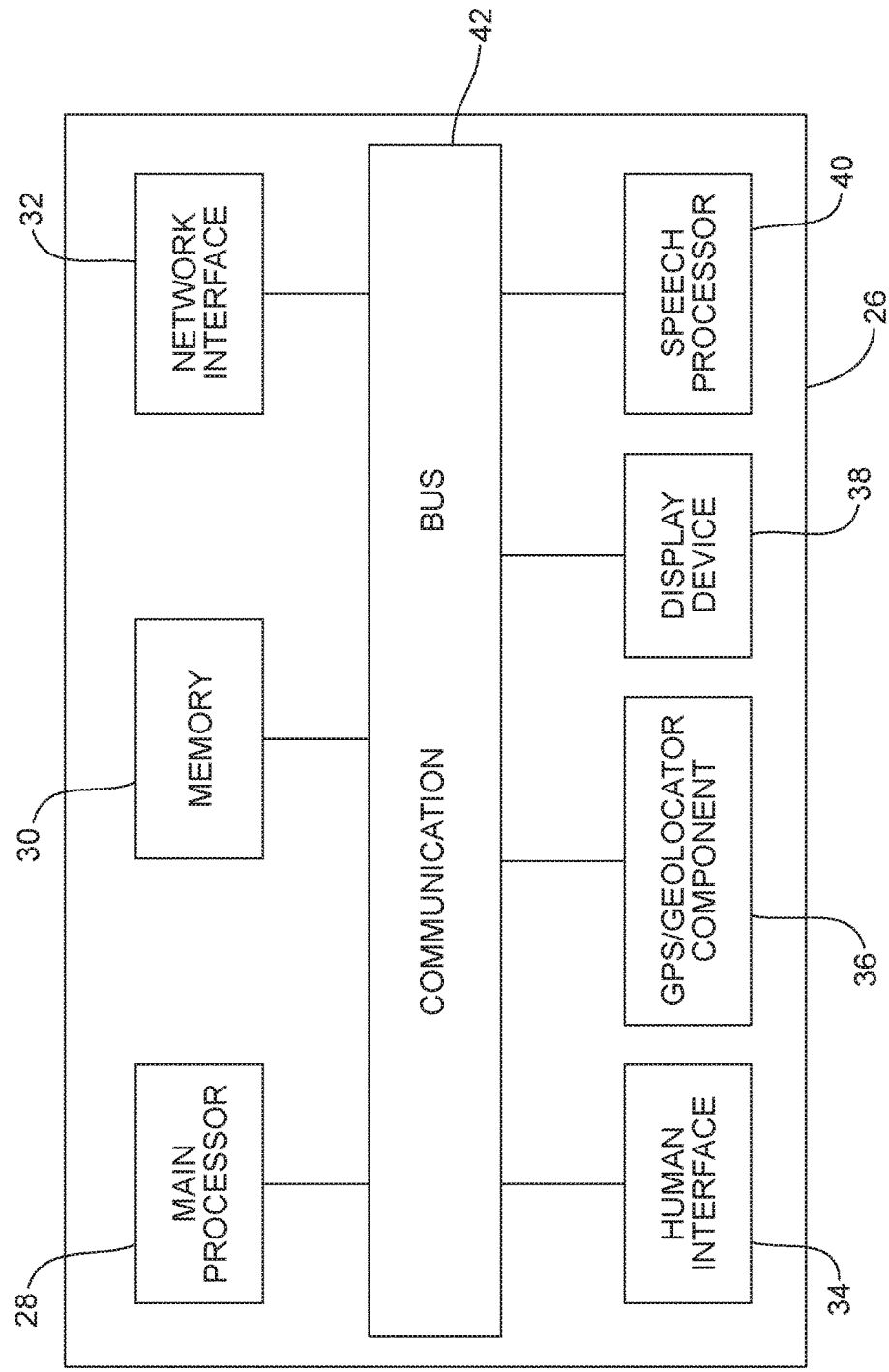
FIG. 2 is a schematic block diagram of a body control module of a type that may be incorporated into the UVB lighting system as illustrated in FIG. 1.

As further illustrated in FIG. 1, the UVB lighting system 10 may also include a controller, such as the body control module (BCM) 26. As best illustrated in FIG. 2, the body control module 26 may comprise a computing device having one or more processors 28, one or more memories 30, one or more network interfaces 32, a human interface 34, a global positioning satellite or GPS/geolocator component 36, a display device such as a multi-function display with touchscreen capability 38, and a speech processor 40 that all communicate with each other over a communication bus 42. The BCM 26 performs a number of interior body electrically-based functions including, for example, interior locking, remote key entry, interior lighting, exterior lighting, windshield wiper control and the like. In some embodiments, the BCM 26 may also function to control entertainment functions (e.g. radio, CD player and communications such as telephone and internet communications over a wireless network). In some embodiments the BCM 26 may be connected by a communication bus (not shown) to one or more additional control modules that provide one or more of these additional functions.

As illustrated in FIG. 1, the BCM 26 is connected to a second lighting module 46 and a third lighting module 48. The second lighting module 46 includes a third UVB light source 50 and a third map light 52. The third lighting module includes a fourth UVB light source 54 and a fourth map light 56. The second lighting module 46 and the third lighting module 48 may be positioned in the motor vehicle so that the UVB light sources 12, 14, 50 and 54 of the three lighting modules 24, 46 and 48 cover most of the human interface surfaces of the passenger compartment of the motor vehicle when the UVB lighting system 10 is activated. Thus, for example, where the first lighting module 24 is positioned in a center roof console immediately behind the windshield, the second lighting module 46 may be positioned over a left rear door or on the left C-pillar while the third lighting module 48 may be positioned over the right rear door or on the right C-pillar.

While the illustrated embodiment includes the three lighting modules 24, 46 and 48, it should be appreciated that the second and third lighting modules 46, 48 are optional. In addition, it should be appreciated that the UVB lighting system 10 may include more than three lighting modules 24, 46, 48 if desired or needed to provide the desired array of UVB lighting.

The three lighting modules 24, 46, 48, including the first UVB light source 12, second UVB light source 14, first map light 16, second map light 18, third UVB light source 50, third map light 52, fourth UVB light source 54 and fourth map light 56 are all under the control of the BCM 26. That BCM 26 may be configured to operate in a number of different ways. For example, the controller or BCM 26 may be configured to activate the UVB light sources 12, 14, 50 and 54 for a predetermined operating cycle and to flash one or more of the map lights 16, 18, 52 and 56 when that operating cycle is completed. Thus, for example, the controller or BCM 26 may activate the UVB light sources 12, 14, 50 and 54 for a period of 10 to 15 minutes upon the operator starting the motor vehicle.

Alternatively, or in addition, the lighting module 24 may include a UVB indicator lamp 58 and a second UVB indicator lamp 60 on the printed circuit board 20 adjacent the respective first UVB light source 12 and second UVB light source 14. In such an embodiment the controller or BCM 26 may be configured to activate the UVB indicator lamps 58, 60 when the first and second UVB light sources 12, 14 are activated so as to provide a visual indication of both (a) UVB light source activation and (b) the interface surfaces upon which the UVB light is directed to the motor vehicle operator.

As further illustrated in FIG. 1, the UVB lighting system 10 may include a child protection device in the form of a seat weight sensor 62 and/or an imaging device, such as a camera 64, such as may be incorporated into an airbag module 66 of the motor vehicle. In such an embodiment, the controller or BCM 26 may be configured to prevent activation of the UVB lighting system 10 when a child is detected in a passenger compartment of the motor vehicle unless the operator overrides this defeat function.

In other possible embodiments, the controller or BCM 26 may be configured to adjust the operating cycle of the UVB light system 10 for makeup and/or sunscreen worn by an occupant of a passenger compartment of the motor vehicle and detected via the imaging device or camera 64. If makeup or sunscreen is detected, the operating cycle may be increased by a predetermined amount to compensate for the UVB screening properties of the make-up or sunscreen.

Figure 3:
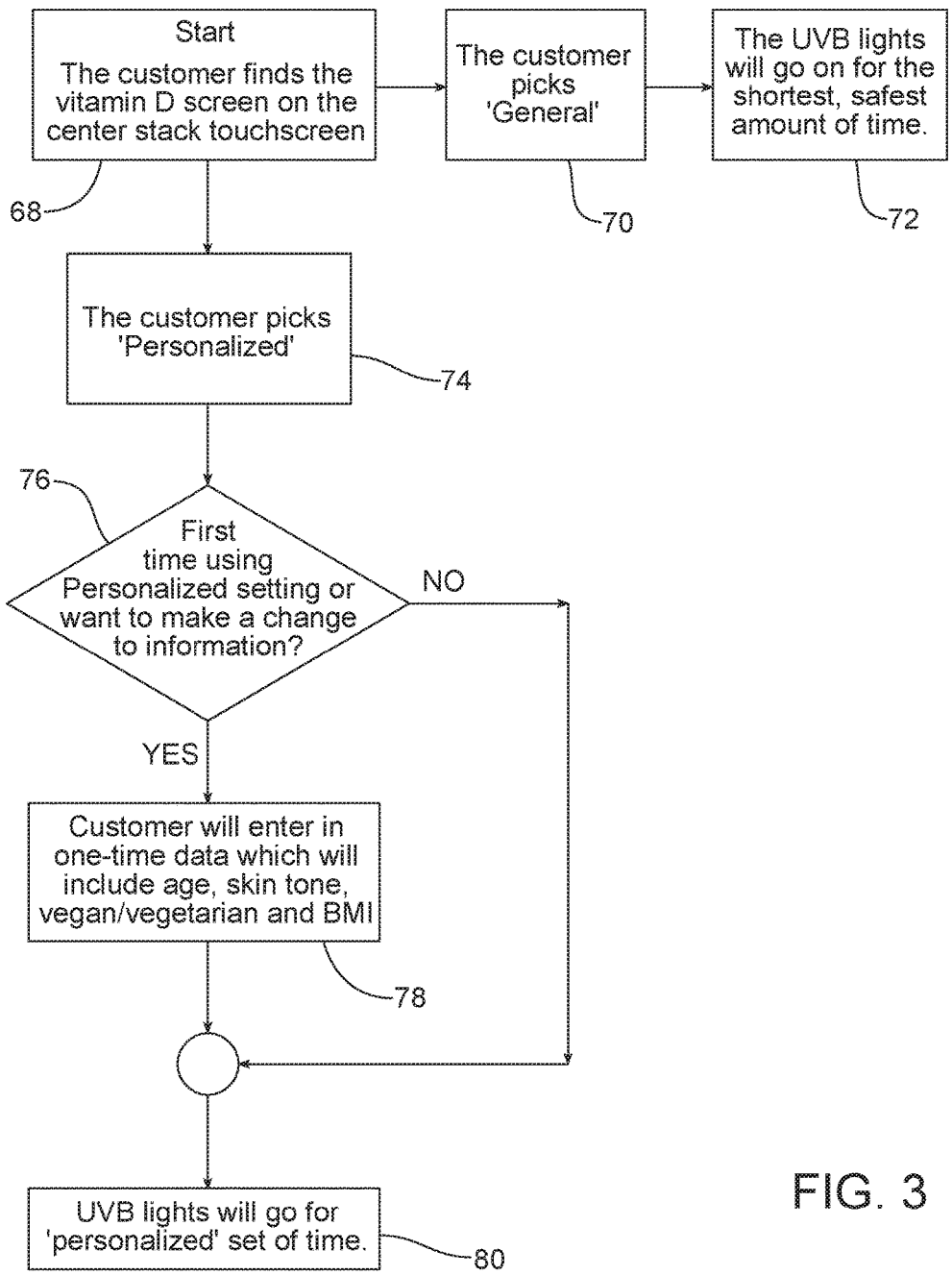
FIG. 3 is a control logic flow diagram for one possible embodiment of the UVB lighting system illustrated in FIG. 1.

In yet another possible embodiment, the controller or BCM 26 may be configured to customize the operating cycle of the UVB lighting to the desires of a particular operator. In this regard, reference is made to FIG. 3 which illustrates one possible control logic flow diagram for the operation of the UVB lighting system 10. In the illustrated embodiment, the operator initially finds the UVB light system operation screen on the display device 38. See Box 68. If the customer selects "general" and does not enter a customized program, (See Box 70) the UVB lighting system 10 is operated for the shortest, safest amount of time (e.g. 10 to 15 minutes). See Box 72.

In contrast, if the user or customer elects to personalize or customize the operation of the UVB lighting system by, for example, depressing the touchscreen customization "button" (See Box 74), the controller or BCM 26 queries the operator through the display device 38 if this is the first time utilizing the personalized setting or if the operator wants to make a change to the personalized setting (See Box 76). In the event this is the first time the operator has attempted to utilize the customized setting or the operator wishes to change existing customization settings, the operator will enter in one-time data by means of the touchscreen display 38. That data will include the user or operator's age, skin tone, diet, BMI and any other appropriate information. See Box 78. The controller or BCM 26 will use that data to formulate the operating cycle for the UVB lighting system 10 ensuring, via an appropriate algorithm, the selection of the most appropriate intensity and/or duration of the UVB operating cycle for the benefit of the operator (See Box 80). If this personalized data has already been input to the controller or BCM 26, the data entry step at Box 78 is skipped and the UVB lighting system is operated for the personalized set time as per Box 80. As described above, the UVB lighting system is personalized or customized utilizing the touchscreen display device 38. Here it should be appreciated that the operator may use voice commands to achieve the same end via the speech processor 40 if desired.

As illustrated in FIG. 4, any one or all of the UVB light sources, 12, 14, 50, 54 may incorporate a plurality of UVB light emitting diodes that are provided in series. Note light emitting diodes (LEDs) $82_1$-$82_6$ illustrated in FIG. 4. As further illustrated in FIG. 4, the UVB lighting system 10 includes a first power input 84 at a first end 86 of the plurality of UVB LEDs $82_1$-$82_6$ and a second power input 88 adjacent a second end 90 of the series of UVB light emitting diodes between UVB LEDs $82_5$-$82_6$.

In such an embodiment as illustrated in FIG. 4, the controller or BCM 26 is configured to feed power to the plurality of UVB light emitting diodes $82_1$-$82_6$: (a) via the first power input 84 for sanitation of the interface surfaces of the passenger compartment of the motor vehicle and (b) via the second power input 88 for promoting vitamin D production in the human occupants of the motor vehicle.

As illustrated in FIG. 5, the peak wavelength of the UVB light emitted by the UVB LEDs $82_1$-$82_6$ varies depending on their operating temperature. The lower the operating temperature, the lower the peak wavelength. As the lower wavelengths provide for better sanitation of the interface surfaces of the passenger compartment, and the UVB LEDs $82_1$-$82_6$ operate at a lower temperature when more of the UVB LEDs are driven in series, this lighting control logic enhances the effectiveness of the sanitation or disinfection of the interface surfaces when this is the desired operator result.

Consistent with the above description, a method is also provided for providing UVB light to a passenger compartment of a motor vehicle. That method comprises the steps of:

(a) locating UVB light source 12, 14, 50, 54 along a roof panel of a motor vehicle, (b) activating, by a controller 26, the UVB light sources for a predetermined operating cycle and flashing, by the controller, a map light 16, 18, 52 and/or 56 when the operating cycle is completed.

Further, the method may also include the step of activating, by the controller 26, a UVB indicator lamp 58 and/or 60, when the UVB light sources 12, 14, 50, 54 are activated. The method may also include the steps of detecting, by a child detection device 62 and/or 64, a child in the passenger compartment of the motor vehicle and preventing, by the controller/BCM 26, activation of the UVB light source 12, 14, 50, 54 when a child is detected.

Still further, the method may include the step of detecting, by a visual imaging device or camera 64, makeup or sunscreen on a face of a vehicle occupant and adjusting, by the controller 26, the predetermined operating cycle of the UVB light source for the detected makeup or sunscreen worn on the face of the vehicle occupant.

Still further, the method may include the step of customizing, by the controller 26, the predetermined operating cycle of the UVB light source or system 10 for a particular operator.

In addition, the method may include operating, by the controller 26, the UVB light source 12, 14, 50, 54 at a first temperature and a first intensity when sanitizing a passenger compartment of the motor vehicle. In addition, the method may include operating, by the controller 26, the UVB light source 12, 14, 50, 54 at a second temperature and a second intensity when promoting the vitamin D production of an occupant of the motor vehicle.

Further, the method may also include the step of confirming, by the controller 26, that the passenger compartment of the motor vehicle is unoccupied and that the passenger compartment doors are locked before activating the UVB light source 12, 14, 50, 54 to sanitize the passenger compartment of the motor vehicle. More specifically, the seat weight person 62 and the imaging device 64 provides data to the controller 26 indicating when the passenger compartment is unoccupied. The door lock modules or related door lock sensors provide data to the controller 26 indicating when all the doors are locked. Here it should be appreciated that activation of the system 10 for the purpose of sanitizing the passenger compartment will be delayed until these two prerequisites (i.e. unoccupied passenger compartment and locked doors) are confirmed.

In summary, the UVB lighting system 10 provides a number of benefits and advantages. The system 10 may be activated via the touch screen display 38 or voice processor 40 thereby eliminating the need for and cost of dedicated switches. The system 10 includes one or more indicator lamps 58, 60 giving a clear visual indication to the operator when the UVB light sources 12, 14, 50, 54 are activated. The flashing map lights 16, 18, 52 and 56 also give a clear indication when a UVB light source activation cycle is completed.

By using several, perhaps 3-6, LEDS $82_1$-$82_6$, connected in series, the intensity of the UVB light sources 12, 14, 50, 54 may be varied. Further, the LEDs $82_1$-$82_6$ may be operated at a hotter or cooler temperature. Thus, by running more LEDs $82_1$-$82_6$ at a lower current, each LED may be run at a cooler temperature which shifts the wavelength of the emitted light down for better sanitation. In contrast, by running only one LED $82_1$-$82_6$ at a higher current and maximum temperature, the wavelength of the emitted light may be shifted up for better vitamin D production.

The child detection device 62, 64 prevents operation of the system 10 by a child. Further, the clock in the motor vehicle may be utilized to limit the UVB dose provided per day from the system 10.

The foregoing has been presented for purposes of illustration and description. It is not intended to be exhaustive or to limit the embodiments to the precise form disclosed. Obvious modifications and variations are possible in light of the above teachings. All such modifications and variations are within the scope of the appended claims when interpreted in accordance with the breadth to which they are fairly, legally and equitably entitled.

What is claimed:

1. A UVB lighting system for a motor vehicle, comprising:
a printed circuit board including a UVB light source and a map light; and
a controller configured to activate said UVB light source for a predetermined operating cycle and to flash said map light when said operating cycle is completed.

2. The UVB lighting system of claim 1, further including a UVB indicator lamp on said printed circuit board, wherein said controller is configured to activate said UVB indicator lamp when said UVB light source is activated so as to provide a visual indication of UVB light source activation.

3. The UVB lighting system of claim 1, further including a child detection device and the controller is connected to said child detection device and configured to prevent activation of said UVB lighting when a child is detected in a passenger compartment of the motor vehicle.

4. The UVB lighting system of claim 3, wherein said child detection device is a seat weight sensor.

5. The UVB lighting system of claim 3, wherein said child detection device is an imaging device.

6. The UVB lighting system of claim 4, further including a visual imaging device and the controller is connected to said visual imaging device and configured to adjust an operating cycle of said UVB lighting system for makeup or sunscreen worn by an occupant of a passenger compartment of said motor vehicle.

7. The UVB lighting system of claim 1, wherein the controller is configured to customize an operating cycle of said UVB lighting system for a particular operator.

8. The UVB lighting system of claim 1, wherein said UVB light source comprises a plurality of UVB light emitting diodes.

9. The UVB lighting system of claim 8, wherein said plurality of UVB light emitting diodes are provided in series.

10. The UVB lighting system of claim 9, including a first power input at a first end of said plurality of UVB light emitting diodes and a second power input between said first end and a second end of said plurality of UVB light emitting diodes.

11. The UVB lighting system of claim 10, wherein the controller is configured to feed power to said plurality of UVB light emitting diodes (a) via said first power input for sanitizing of a passenger compartment of the motor vehicle and (b) via said second power input for promoting vitamin D production.

12. A method of providing UVB lighting in a motor vehicle, comprising:
locating a UVB light source along a roof panel of the motor vehicle;
activating, by a controller, said UVB light source for a predetermined operating cycle; and
flashing, by said controller, a map light when said operating cycle is completed.

13. The method of claim 12, including activating, by said controller, a UVB indicator lamp when said UVB light source is activated so as to provide a visual indication of UVB light source activation.

14. The method of claim 12, including detecting, by a child detection device, a child in a passenger compartment of the motor vehicle and preventing by said controller, activation of said UVB light source when a child is detected.

15. The method of claim 12, including detecting, by a visual imaging device, makeup or sunscreen on a face of a vehicle occupant and adjusting, by said controller, the predetermined operating cycle of said UVB light source for detected makeup or sunscreen worn on said face by said vehicle occupant.

16. The method of claim 12, including customizing, by said controller, said predetermined operating cycle of said UVB light source for a particular operator.

17. The method of claim 12, including, operating, by said controller, said UVB light source at a first temperature and a first intensity when sanitizing a passenger compartment of said motor vehicle.

18. The method of claim 17, including, operating, by said controller, said UVB light source at a second temperature and a second intensity when promoting vitamin D production of an occupant of the motor vehicle.

19. The method of claim 12, including confirming, by said controller, that said motor vehicle is unoccupied and locked before activating said UVB light source to sanitize a passenger compartment of said motor vehicle.

20. A UVB lighting system for a motor vehicle, comprising:
a printed circuit board including a UVB light source and a map light;
a UVB indicator lamp on said printed circuit board; and
a controller configured to activate said UVB indicator lamp when said UVB light source is activated so as to provide a visual indication of UVB light source activation.

* * * * *